United States Patent [19]

Seemuth

[11] 4,421,522

[45] Dec. 20, 1983

[54] DIESEL FUEL COMPOSITION

[75] Inventor: Paul D. Seemuth, Oak Park, Mich.

[73] Assignee: Ethyl Corporation, Richmond, Va.

[21] Appl. No.: 433,160

[22] Filed: Oct. 6, 1982

[51] Int. Cl.³ .............................................. C10L 1/22
[52] U.S. Cl. ........................................ 44/53; 44/56; 44/57; 44/63; 544/162
[58] Field of Search .................... 44/53, 56, 63, 57; 544/162

[56] References Cited

U.S. PATENT DOCUMENTS

| | | |
|---|---|---|
| 2,484,395 | 10/1949 | Wachter et al. ................. 544/162 |
| 2,905,540 | 9/1959 | Schickh et al. ................. 44/57 |
| 4,198,931 | 4/1980 | Malec ............................ 44/56 |
| 4,204,481 | 5/1980 | Malec ............................ 44/56 |
| 4,227,889 | 10/1980 | Perilstein ...................... 44/56 |
| 4,248,182 | 2/1981 | Malec ............................ 44/56 |
| 4,359,324 | 11/1982 | Elsea, Jr. et al. .............. 44/57 |

*Primary Examiner*—John Doll
*Assistant Examiner*—Mrs. Y. Harris-Smith
*Attorney, Agent, or Firm*—Donald L. Johnson; John F. Sieberth; Joseph D. Odenweller

[57] ABSTRACT

Cetane number of diesel fuel is increased by the addition of a 4-morpholine ethanol nitrate.

5 Claims, No Drawings

DIESEL FUEL COMPOSITION

BACKGROUND

Diesel engines operate by compression ignition. They have compression ratios in the range of 14:1 to 17:1 or higher and for that reason obtain more useful work from a given amount of fuel compared to an Otto cycle engine. Historically, diesel engines have been operated on a petroleum-derived liquid hydrocarbon fuel boiling in the range of about 300°–750° F. Recently, because of dwindling petroleum reserves, alcohol and alcohol-hydrocarbon blends have been studied for use as diesel fuel.

One major factor in diesel fuel quality is cetane number. Cetane number is related to ignition delay after the fuel is injected into the combustion chamber. If ignition delays too long, the amount of fuel in the chamber increases and upon ignition results in a rough running engine and increased smoke. A short ignition delay results in smooth engine operation and decreases smoke. Commercial petroleum diesel fuels generally have a cetane number of about 40–55. Alcohols have a much lower cetane value and require the addition of a cetane improver for successful engine operation.

Through the years, many types of additives have been used to raise the cetane number of diesel fuel. These include peroxides, nitrites, nitrates, nitrosocarbamates, and the like. Alkyl nitrates such as amyl nitrate, hexyl nitrate and mixed octyl nitrates have been used commercially with good results.

SUMMARY

It has now been discovered that the cetane rating of diesel fuel, both hydrocarbon and alcohols or mixtures thereof, can be increased by the addition of a 4-morpholine ethanol nitrate ester.

DESCRIPTION OF PREFERRED EMBODIMENTS

A preferred embodiment of the invention is a liquid fuel adapted for use in a diesel engine, said fuel being selected from the group consisting of liquid hydrocarbons of the diesel boiling range, alcohols and mixtures thereof, said fuel containing a cetane number increasing amount of a fuel soluble 4-morpholine alkanol nitrate. Such compounds contain in their structure the group

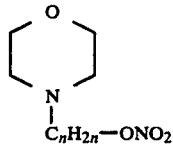

wherein n is an integer from 1 to about 20, more preferably about 1–4. The morpholine heterocyclic ring may be substituted with any of a broad range of substituents as long as they do not render the compound insoluble in diesel fuel.

A still more preferred group of additives have the structure

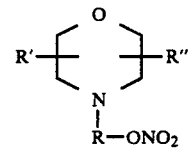

wherein R is a divalent hydrocarbon group containing 1–20 carbon atoms, and R' and R" are independently selected from the group consisting of hydrogen, alkyls containing 1–20 carbon atoms, cycloalkyl containing 5–8 carbon atoms, alkenyl containing 2–20 carbon atoms, aryl containing 6–12 carbon atoms, and aralkyl containing 7–12 carbon atoms.

Representative examples of these additives are:
4-(2-methylmorpholine) ethanol nitrate
4-(3-isooctylmorpholine) ethanol nitrate
4-(3-eicosylmorpholine) butanol nitrate
4-(3-cyclopentylmorpholine) hexanol nitrate
4-(2-cyclohexylmorpholine) octanol nitrate
4-(2-cyclooctylmorpholine) dodecanol nitrate
4-(2-propenylmorpholine) propanol nitrate
4-(3-dodecenylmorpholine) ethanol nitrate
4-(3-eicosenylmorpholine) ethanol nitrate
4-(2-phenylmorpholine) ethanol nitrate
4-(3-naphthylmorpholine) butanol nitrate
4-(3-benzylmorpholine) butanol nitrate
4-(2-(α-methylbenzyl)morpholine) ethanol nitrate
4-[3-(4-isohexylphenyl)morpholine] ethanol nitrate
and the like.

In a more preferred embodiment, both R' and R" in the above structure are hydrogen and R is a divalent hydrocarbon group containing about 1–4 carbon atoms. These compounds include
4-morpholine ethanol nitrate
4-morpholine-(2-methylethanol) nitrate
4-morpholine methanol nitrate
4-morpholine-butanol nitrate.

The most preferred additive is 4-morpholine ethanol nitrate which has the structure

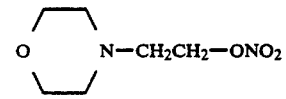

This preferred compound is reported by J. Barbiere in *Bull. Soc. Chim.* 11, p.470 (1944).

The additives can readily be prepared by nitration of the corresponding 4-morpholine alkanol compound by standard procedures such as by use of mixed sulfuric-nitric acid or acetic anhydride-nitric acid. The 4-morpholine alkanol is added to the rapidly stirred mixed acid at low temperature such as −20° to 10° C., more preferably, about −15° C. to 0° C.

EXAMPLE 1

In a reaction vessel was placed 28 ml. conc. sulfuric acid. To this was added 25 g. of N-ethanol morpholine to form the ammonium salt. In a second vessel was placed a solution of 14.8 ml. conc. nitric acid and 22 ml. conc. sulfuric acid. The mixed acid was cooled to −14° C. The above N-ethanol morpholine salt was added to this over a two-hour period. The temperature was allowed to rise to the 6.6°–7.2° C. range. The reaction mixture was stirred an additional 30 minutes and then poured into an ice-water mixture. The aqueous solution was neutralized to pH 8 using sodium carbonate. An upper organic layer formed. The entire mixture was extracted twice with 150 ml. portions of diethyl ether. The ether extract was dried over magnesium sulfate and the ether removed under vacuum. The product formed a viscous gel which was soluble in diesel fuel. The product was identified by IR and NMR as 4-morpholine ethanol nitrate.

Other 4-morpholine alkanol nitrate esters can be made by following the above general procedure.

The amount of cetane improver added depends on the type of fuel being used, the initial cetane value, and the amount of cetane number increase desired. Alcohol fuels such as methanol, ethanol, isopropanol, isobutanol, hexanol, and the like, have very low cetane values and large amounts of cetane improvers are required. A useful range in which to operate is about 5-25 weight percent cetane improver.

Blends of alcohol and petroleum-derived diesel fuel have higher cetane values and require less cetane improver. A useful range is about 0.5-10 weight percent.

Petroleum-derived distillate fuels in the diesel boiling range require only small amounts of cetane improver to achieve a significant increase in cetane number. Such fuels without any cetane improver generally have cetane numbers in the range of about 25-60. Cetane numbers in the range of 25-35 are considered low and those in the range of 50-60 are considered top grade diesel fuels. Diesel fuels in the 35-50 mid-range are most common. An object of the invention is to upgrade the low cetane number fuels at least into the mid-range and to increase the cetane value of the mid-range fuels into the upper portion of the mid-range (e.g. 45-50) or even into the premium range above 50. It has been found that highly beneficial results can be achieved using as little as 0.05 weight percent of the present additive. Accordingly, a useful concentration range in petroleum derived diesel fuel is about 0.01-5 weight percent and more preferably about 0.05-0.5 weight percent.

The cetane increase caused by the present additives was measured in comparison to that caused by a commercial cetane improver, isooctyl nitrate. The fuel was a blend of 26 cetane number light cycle oil and 46 cetane number diesel fuel giving a 38 cetane number blend.

| Concentration | Isooctyl Nitrate | 4-Morphone ethanol Nitrate |
|---|---|---|
| None | 38.0 | 38.0 |
| 0.05 | 39.3 | 40.07 |
| 0.1 | 40.5 | 41.01 |
| 0.15 | 41.8 | 41.19 |

These results show that the new additives are very effective in raising the cetane number of diesel fuel.

Other conventional additives may be included in the diesel fuel including antioxidants, cold flow improvers, cold filter plugging inhibitors, detergents, rust inhibitors, and the like, including other cetane improvers.

I claim:

1. Liquid fuel adapted for use in a diesel engine, said fuel being selected from the group consisting of liquid hydrocarbons of the diesel boiling range, alcohols and mixtures thereof, and said fuel containing a cetane number increasing amount of a fuel soluble 4-morpholine alkanol nitrate.

2. A composition of claim 1 wherein said fuel is a liquid hydrocarbon of the fuel boiling range.

3. A composition of claim 2 wherein said 4-morpholine alkanol nitrate has the structure

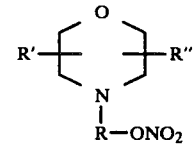

wherein R is a divalent hydrocarbon group containing 1-20 carbon atoms, and R' and R" are independently selected from the group consisting of hydrogen, alkyls containing 1-20 carbon atoms, cycloalkyl containing 5-8 carbon atoms, alkenyl containing 2-20 carbon atoms, aryl containing 6-12 carbon atoms, and aralkyl containing 7-12 carbon atoms.

4. A composition of claim 3 wherein R' and R" are hydrogen.

5. A composition of claim 4 wherein R is the group —$CH_2CH_2$—.

* * * * *